United States Patent

Kerr

[11] Patent Number: 5,941,896
[45] Date of Patent: Aug. 24, 1999

[54] FILTER AND METHOD FOR TRAPPING EMBOLI DURING ENDOVASCULAR PROCEDURES

[75] Inventor: Andrew Kerr, New York, N.Y.

[73] Assignee: Montefiore Hospital and Medical Center, Bronx, N.Y.

[21] Appl. No.: 08/991,469

[22] Filed: Dec. 16, 1997

Related U.S. Application Data

[60] Provisional application No. 60/058,121, Sep. 8, 1997.

[51] Int. Cl.$^6$ .................................................. A61M 29/00
[52] U.S. Cl. ............................................ 606/200; 606/192
[58] Field of Search ..................................... 606/159, 200, 606/192, 106, 110, 113, 114, 127, 128, 151

[56] References Cited

U.S. PATENT DOCUMENTS

| | | |
|---|---|---|
| 3,540,431 | 11/1970 | Mobin-Uddin . |
| 3,952,747 | 4/1976 | Kimmell, Jr. . |
| 4,619,246 | 10/1986 | Molgaard-Nielsen et al. . |
| 4,790,812 | 12/1988 | Hawkins, Jr. et al. . |
| 4,873,978 | 10/1989 | Ginsburg . |
| 5,053,008 | 10/1991 | Bajaj ........................................ 604/104 |
| 5,143,082 | 9/1992 | Kindberg et al. ........................ 128/749 |
| 5,147,371 | 9/1992 | Washington et al. .................... 606/127 |
| 5,324,304 | 6/1994 | Rasmussen . |
| 5,329,942 | 7/1994 | Gunther et al. . |
| 5,549,626 | 8/1996 | Miller et al. ............................. 606/200 |
| 5,800,457 | 9/1998 | Gelbfish .................................. 606/200 |

*Primary Examiner*—Michael Buiz
*Assistant Examiner*—Vy Q. Bui
*Attorney, Agent, or Firm*—Anthony J. Casella; Gerald E. Hespos; Ludomir A. Budzyn

[57] ABSTRACT

A filter and method for trapping emboli during endovascular procedures are provided. In one embodiment of the invention, the filter is formed from a bent, flexible guidewire shaped to define a frame and a porous filtering material mounted to portions thereof. In a collapsed state, the filter can readily pass through the lumen of a catheter and into the bloodstream of a patient. Upon completion of an endovascular procedure, the filter is collapsed and retracted into the catheter. In alternative embodiments of the invention, porous filtering material is mounted to external portions of a catheter, and a control guidewire is provided to selectively expand the filter between open and closed states.

13 Claims, 5 Drawing Sheets

FILTER AND METHOD FOR TRAPPING EMBOLI DURING ENDOVASCULAR PROCEDURES

This application claims the benefit of Provisional Application No. 60/058,121 filed Sep. 8, 1997.

BACKGROUND OF THE INVENTION

1. Field of the Invention

This invention relates to a blood filter and method of using thereof for trapping and removing emboli during an endovascular procedure.

2. Description of the Prior Art

Advances in medicine and technology are leading to development of minimally invasive surgical techniques for treatment of various medical conditions. For example, stenosis formed in a blood vessel may be treated endovascularly using techniques such as balloon angioplasty, stent placement, or thrombolysis. However, the use of such endovascular techniques has been limited due to embolization of debris from the treated portion of the vessel to a downstream portion resulting in complications. For example, treatment of a stenosis in a carotid artery can result in ischemic complications and possible embolic stroke. Thus, there is a need for a device to trap emboli which may result from endovascular treatment of a blood vessel.

Many blood filters are in the prior art which are formed to trap emboli. A number of permanently implantable blood filters were developed in the prior art for capturing clots developed post-operatively in a patient subjected to extensive periods of bed rest. These filters are intended to be implanted in the inferior vena cava to prevent the passage of clots into the lungs. For example, U.S. Pat. No. 3,540,431 to Mobin-Uddin, entitled "COLLAPSIBLE FILTER FOR FLUID FLOWING IN CLOSED PASSAGEWAY", discloses an umbrella-shaped filter which is spring biased to have an open configuration in its natural state. Upon release from an introducer catheter into the inferior vena cava, the Mobin-Uddin filter springs into an open configuration with the spokes of the filter being in pressing engagement with the vessel wall. A second example of a permanently implantable blood filter is disclosed in U.S. Pat. No. 3,952,747 to Kimmell, Jr., entitled "FILTER AND FILTER INSERTION INSTRUMENT", also known as the Greenfield-Kimray filter. The Greenfield-Kimray filter comprises a plurality of spring biased bent wires extending from a single central hub. Upon ejection from an introducer instrument into a blood vessel, the Greenfield-Kimray filter expands to engage the wall of the vessel. Generally, the permanently implantable blood filters are configured to trap life-threatening emboli, considered to be 3 mm or larger in diameter. The trapped emboli are broken down by blood passing through the respective filter, with the emboli eventually being eroded to a harmless size. It can be appreciated, other than through surgical removal, no practical method is disclosed for removing permanently implantable blood filters. Thus, this type of blood filter would have to be left in a blood vessel if used during an endovascular procedure, which may be undesirable.

Retrievable blood filters are also known in the prior art which can be removed through the blood vessel without requiring surgery. Some examples are U.S. Pat. No. 4,619,246 to Molgaard-Nielsen et al., entitled "COLLAPSIBLE FILTER BASKET", and U.S. Pat. No. 5,329,942 to Gunther et al., entitled "METHOD FOR FILTERING BLOOD IN A BLOOD VESSEL OF A PATIENT".

U.S. Pat. No. 4,873,978 to Ginsburg, entitled "DEVICE AND METHOD FOR EMBOLI RETRIEVAL", discloses a retrievable blood filter for trapping and removing emboli from a blood vessel, during and after an endovascular procedure. Ginsburg discloses a collapsible filter which is introduced, via a catheter in an upstream direction in a blood vessel to a location downstream from a stenosis which is to be treated. A stenosis treatment device is introduced, via a second catheter, in a downstream direction to the stenosis. Any emboli dislodged during the treatment of the stenosis travel downstream in the blood vessel and are trapped in the Ginsburg filter. The Ginsburg filter is collapsed and removed after treatment is completed with any trapped emboli being removed therewith. It is readily apparent, however, that the required insertion of two separate catheters into a patient to complete treatment and blood filtering is a drawback of the Ginsburg filter.

It is an object of the subject invention to provide a collapsible filter for trapping emboli during and after an endovascular procedure.

It is also an object of the subject invention to provide a method for filtering blood during an endovascular procedure for the trapping and removal of emboli therefrom.

SUMMARY OF THE INVENTION

The above-stated objects are met by a blood-filtering device comprised of a bent guidewire and a filtering material. The guidewire is of any type known by those skilled in the art to be flexible and resilient, such as an angiographic guidewire. In all of the embodiments of the invention, one end of the guidewire is formed as a loop. In a relaxed state, the guidewire extends from the loop, to define a generally circular shape, and then through the loop, in a hitch configuration. The length of the guidewire extending from the loop and into the loop, which length defines the generally circular shape, is selectively adjustable by correspondingly urging the guidewire in or out of the loop. The resiliency of the guidewire enables the generally circular shape to be maintained in a relaxed state.

In all of the embodiments of the invention, the filtering material is selected to have interstices dimensioned to allow the passage of blood but prevent the passage of life-threatening emboli. A porous fabric, such as DACRON® or LYCRA®, or a fine-mesh net may be used as the filtering material. The filtering material is slidably connected to the length of the guidewire which defines the generally circular shape such that the filtering material will not be drawn through the loop of the guidewire upon adjustment of the guidewire through the loop. As such, the filtering material may be formed with a plurality of connecting loops through which the portion of the guidewire defining the generally circular shape is threaded. The connecting loops are slidable relative to the guidewire such that the spacing between the connecting loops is varied depending on the extent the guidewire is caused to define the generally circular shape. With the guidewire in a relaxed state, the connecting loops will be separated by the greatest degree of spacing, with the filtering material being stretched. With a significant portion of the guidewire having been urged in through the loop formed by the guidewire, the connecting loops will be bunched together with the filtering material being collapsed. Alternatively, a continuous hem can be formed on the filtering material dimensioned to allow the passage of the length of guidewire defining the circular shape therethrough, with the guidewire being in a relaxed state.

In a first embodiment of the invention, the guidewire is bent to define a first straight length extending angularly from the generally circular shape, and a second straight length extending from the first straight length. The second straight length extends through the generally circular shape into a catheter with the two straight lengths defining an acute angle therebetween. The resiliency of the guidewire enables this shape to be maintained in a relaxed state. The filtering material is extended to cover the union of the two straight lengths, whereby the filter has a generally conical shape.

As an example of a possible use, the first embodiment of the filter is collapsed and disposed into a catheter with the union of the first and second straight lengths of the guidewire pointing in the direction of insertion of the catheter. Using fluoroscopic techniques, the distal end of the sheath is located slightly downstream in the blood vessel relative to the stenosis which is to be treated. After removal of the dilator from the distal end of the sheath, the filter is urged therefrom. Upon release from the sheath, the filter assumes its relaxed state, with the length of the guidewire defining the circular shape being in pressing engagement with the blood vessel wall. The sheath is then retracted slightly to a location upstream of the stenosis and endovascular treatment can be had.

The guidewire used to form the filter of the first embodiment of the subject invention can also be simultaneously used to guide an angioplasty balloon or stent to the stenosis which is to be treated. Any emboli dislodged during the treatment of the stenosis will be trapped by the filter of the subject invention. Once the endovascular treatment is completed, the treatment device is retracted along the guidewire. Thereafter, the guidewire is caused to be retracted, thereby causing a collapse of the filter, with any trapped emboli being caught therein. The filter and entrapped emboli are removed through the catheter.

It can be appreciated that the first embodiment of the invention is only intended for use in a situation where the filter assembly is introduced in a downstream direction relative to the stenosis which is to be treated, such as when treating a stenosis in the carotid artery through a femoral puncture site. Situations may arise, however, where the filtering device practically may be only introduced in an upstream direction relative to a stenosis which is to be treated. For example, endovascular treatment of a stenosis in either the left or right iliac artery may be desired through a femoral puncture site. To this end, a second embodiment of the invention is provided in which the guidewire is formed to extend from the generally circular shape, through the loop and into a catheter. The filtering material, as in the first embodiment, is slidably connected along the portion of the guidewire defining the generally circular shape, but pulled to extend in the opposite direction. In the first embodiment of the invention, the filtering material is disposed to trap emboli travelling in a direction away from the introducer catheter, whereas, in the second embodiment, the filtering material is disposed to trap emboli travelling in a direction towards the introducer catheter.

By example, in use, with the distal end of an introducer catheter being located slightly downstream in the bloodstream relative to a stenosis, a stenosis treatment device is introduced into the bloodstream. Thereafter, the filter of the second embodiment of the invention is caused to be collapsed and passed through the lumen of the introducer catheter. The guidewire of the filter is urged through the catheter until the filter is expulsed therefrom. Upon expulsion, the filter acquires its relaxed state with a portion of the guidewire defining the generally circular shape being in pressing engagement with the wall of the blood vessel. Once treatment has been completed, the guidewire is held in a fixed position and the catheter is advanced relative thereto. As the catheter advances, the catheter comes into pressing engagement with the loop defined by the guidewire and a collapse of the filter ensues upon withdrawal of the guidewire. The collapsed filter is eventually forced into the lumen of the sheath with trapped emboli being carried away therewith.

In a third embodiment of the invention, the filter is mounted to an angioplasty catheter. An angioplasty balloon may be provided adjacent the distal end of the catheter with the filter being located proximally along the length of the catheter relative to the angioplasty balloon. An aperture is formed through the wall of the catheter to create a passageway in communication with the lumen of the catheter and the guidewire forming the filter is passed therethrough. The generally circular shape defined by the guidewire encompasses a circumference of the catheter and extends between the aperture and the loop defined at the distal end of the guidewire. The filtering material is slidably connected along the portion of the guidewire defining the generally circular shape and to points on the catheter located proximally relative to the aperture formed through the catheter wall. By applying a force in the proximal direction to the guidewire, the filter is caused to be in a collapsed state, wherein the filtering material is pressed against the outer surface of the catheter. Without the pulling force being applied to the guidewire, the filter assumes a relaxed state, wherein the portion of the guidewire defining the generally circular shape comes into pressing engagement with the wall of the blood vessel and the filtering material is caused to extend between the outer surface of the catheter and the portion of the guidewire engaging the wall of the blood vessel.

The third embodiment of the invention is intended to treat a stenosis to which access is obtained by travelling upstream through a blood vessel. During treatment, the filter is in a relaxed state and any dislodged emboli will be trapped by the filter. Upon completion of treatment, the filter is caused to collapse, thereby trapping emboli, and the entire catheter assembly is removed.

As a fourth embodiment of the invention, to enable treatment in the carotid artery, the filter may be formed on an angioplasty catheter, as described with respect to the third embodiment, but located between the angioplasty balloon and the distal end of the angioplasty catheter. Also, the filtering material must be secured to the outer surface of the catheter adjacent the distal end of the catheter, and the aperture through the catheter wall must be formed adjacent the angioplasty balloon. Otherwise, the structure and operation of the fourth embodiment of the invention is the same as that of the third embodiment of the invention. Accordingly, the fourth embodiment of the invention can be utilized where the invention is introduced in a downstream direction relative to a stenosis.

It is to be understood that, although the operation of the invention has been described with respect to the endovascular treatment of a stenosis, the invention can be used in conjunction with any type of endovascular treatment or merely as a retrievable blood filter. For example, during treatment of an aneurysm through the endovascular placement of a stent-reinforced vascular graft, the subject invention may be employed to filter blood and trap any emboli generated during such a procedure. Also, the filter may be employed in a situation where a high probability of a blood clot being formed is present, such as with a patient subjected to extensive periods of post-operative bedrest. The invention may be incorporated onto a guidewire or onto a catheter for trapping emboli during endovascular procedures (including, but not limited to, angioplasty, stent placement, graft stent placement, thrombolytic drug infusion, transcatheter thrombectomy and ultrasonic thrombectomy) or may be incorporated onto a stent placed within a vessel for short or long term filtering of emboli originating from the heart or from diseased blood vessels. As mounted onto a stent, the filter may be permanently implanted in a patient to reduce the risk of embolic stroke. Further, the device incorporated on a guidewire or a catheter may be used as a stand-alone percutaneous thrombectomy device.

These and other features of the invention will be better understood through a study of the following detailed description and accompanying drawings.

DETAILED DESCRIPTION OF THE INVENTION

Figure 1:
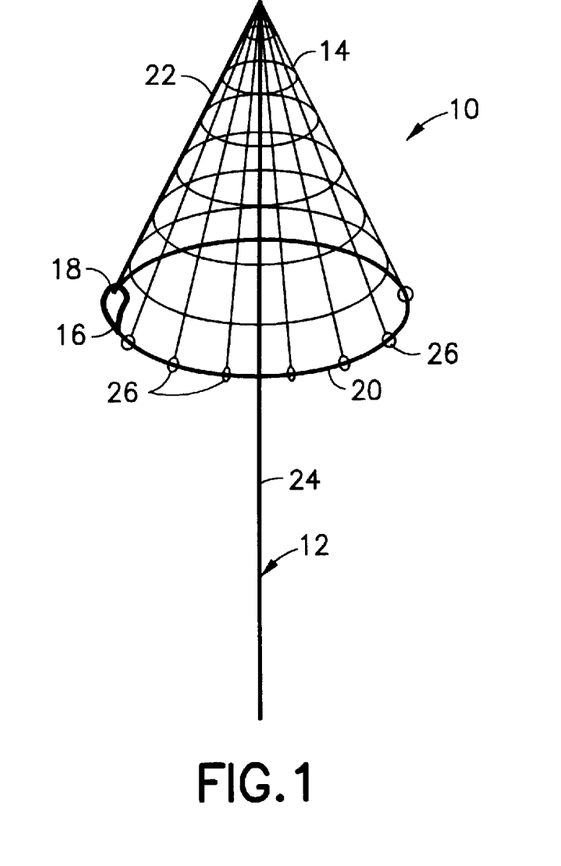
FIG. 1 is an plan view of the filter of the first embodiment of the invention.
Figure 2:
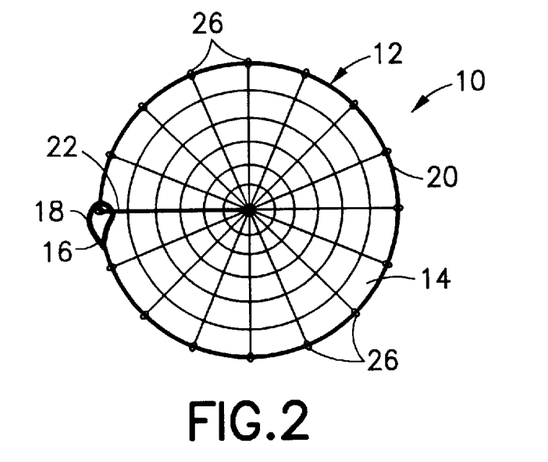
FIG. 2 is a top plan view of the filter of the first embodiment of the invention.
Figure 3:
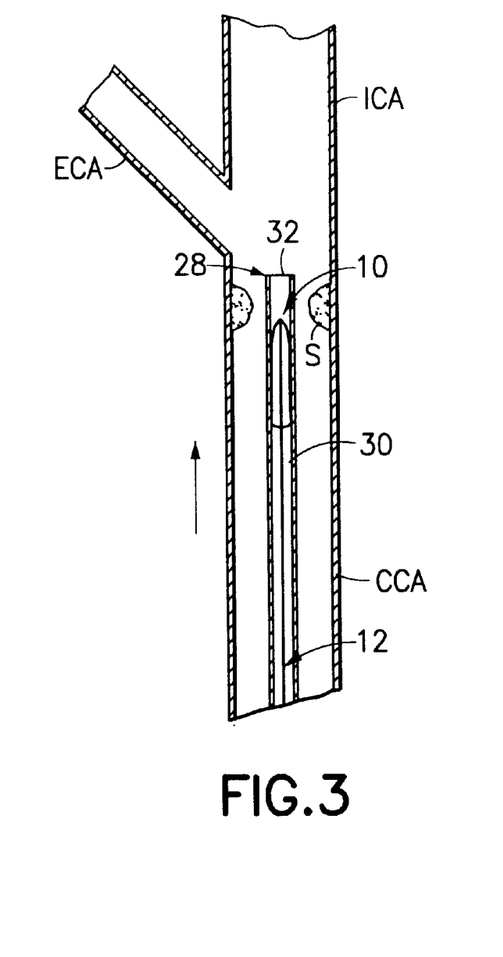
FIGS. 3–7 show the procedure of treating a stenosis formed in the common carotid artery using the first embodiment of the invention.

With respect to the first embodiment of the invention, referring to FIGS. 1 and 2, a filter 10 is provided formed by a guidewire 12 and a filtering material 14. The guidewire 12 is of any type known by those skilled in the art to be flexible and resilient, such as an angiographic guidewire. A distal end 16 of the guidewire 12 is bent and secured to a point on the guidewire 12 to define a loop 18. A length 20 of the guidewire 12 extends from the loop 18 and into the loop 18, in a hitch configuration. The length 20 is formed to define a generally circular shape, with the guidewire 12 being in a relaxed state. A first straight segment 22 extends from the length 20, and a second straight segment 24 extends therefrom. The straight segments 22 and 24 define an acute angle therebetween. The length of the second straight segment 24 must be greater than the length of the introducer catheter, with which the filter 10 is intended to be deployed, to allow a physician to have control over the filter 10, as described below. The resiliency of the guidewire 12 enables the guidewire 12 to assume a relaxed state, which is the shape described above and depicted in FIGS. 1 and 2.

The filtering material 14 is preferably a porous fabric, but may alternatively be a fine-mesh net. The filtering material 14 is slidably connected to the length 20 of the guidewire 12 such that withdrawal and advancement of the length 20 through the loop 18 will cause the filtering material 14 to bunch or expand accordingly. A plurality of connecting loops 26 may be provided with the filtering material 14 to allow slidable connection thereof with the guidewire 12, with the length 20 of the guidewire 12 being threaded through the connecting loops 26. Alternatively, a continuous hem (not shown) may be formed along the edge of the filtering material 14 and the length 20 threaded therethrough. The filtering material 14 must be slidably connected to the length 20 of the guidewire 12 such that the length 20 can be adjusted without the filtering material ever passing through the loop 18.

Referring to FIGS. 3–7, there is depicted diagrammatically an exemplary procedure for treating a stenosis S located in the common carotid artery CCA. An introducer catheter 28 is provided having a lumen 30 formed throughout the entire length thereof. The filter 10 is disposed within the lumen 30 in a collapsed state with the union of the two straight lengths 22 and 24 pointing in the insertion direction. A distal end 32 of the catheter 28 is introduced into a patient's body through a femoral puncture site and directed into the CCA. Using techniques known by those skilled in the art, such as fluoroscopy, the distal end 32 of the catheter is located to be slightly downstream from the stenosis S. The arrows shown in FIGS. 3–7 depict the direction of blood flow. With respect to the first embodiment of the invention, the catheter 28 is introduced in the same direction as the blood flow. As is readily apparent, the distal end 32 of the catheter 28 must pass the stenosis S to reach the desired location. Thus, it is preferred that a low profile catheter be utilized with the subject invention to minimize the possibility of creating emboli prior to treatment of the stenosis S.

Figure 4:
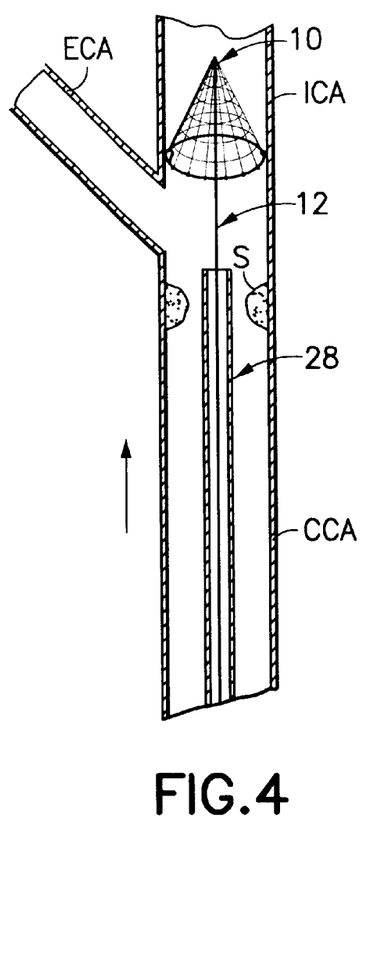

With the distal end 32 of the catheter 28 being in the desired location, the filter 10 is caused to be urged from the lumen 30 through advancement of the guidewire 12 relative to the catheter 28. With the filter 10 being clear of the catheter 28, the filter 10 assumes its relaxed state. As the filter 10 expands to the relaxed state, the length 20 of the guidewire 12 will come into pressing engagement with the wall of the blood vessel, as shown in FIG. 4. To ensure secure placement of the filter 10 relative to the blood vessel, the diameter of the circular shape defined by the length 20 in a relaxed state should be formed to be slightly greater than the inner dimension defined by a blood vessel. In this manner, the expansion of the filter 10 into the relaxed state will generate a pressing force applied to the blood vessel by the length 20.

Figure 5:
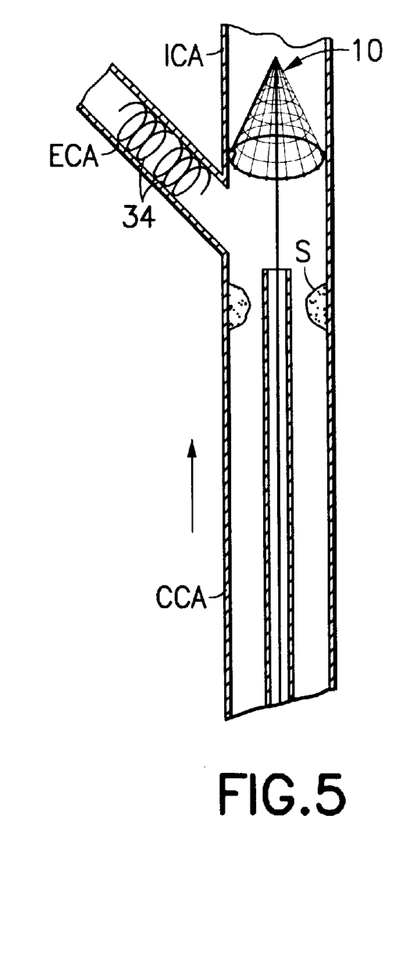

In the exemplary procedure shown in FIGS. 3–7, the filter 10 is located downstream from a branch, which divides the CCA into the internal carotid artery ICA and the external carotid artery ECA. If the stenosis S is not located slightly upstream from a branch forming two blood vessels, the filter 10 alone will be sufficient to trap emboli which may be dislodged during the treatment of the stenosis S. However, as shown in FIGS. 3–7, if the stenosis S is located proximate a branch, precautions should be taken to trap emboli which may travel in either of the blood vessels. One possible approach, although not shown in the Figures, is to provide a second filter 10 through the catheter 28 which will be directed into the ECA and deployed therein. Alternatively, as shown in FIG. 5, spring embolus coils 34, which are known in the prior art, may be disposed in the ECA.

Figure 6:
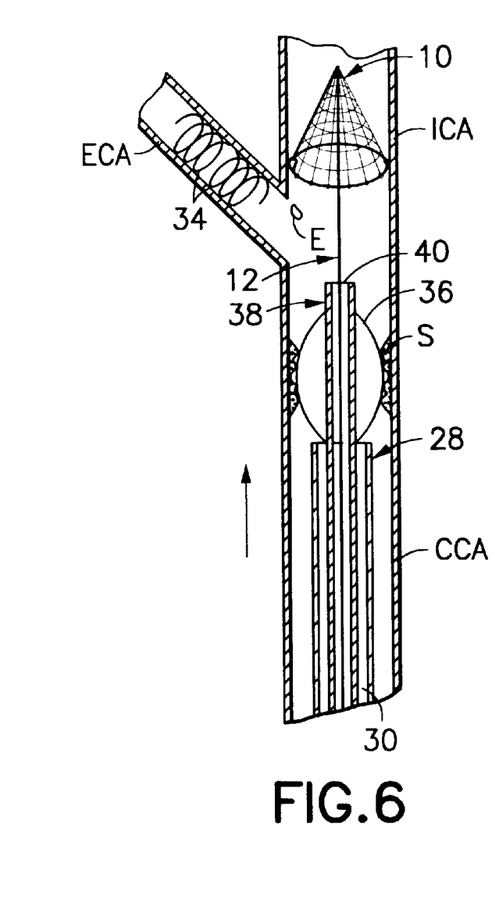
Figure 7:
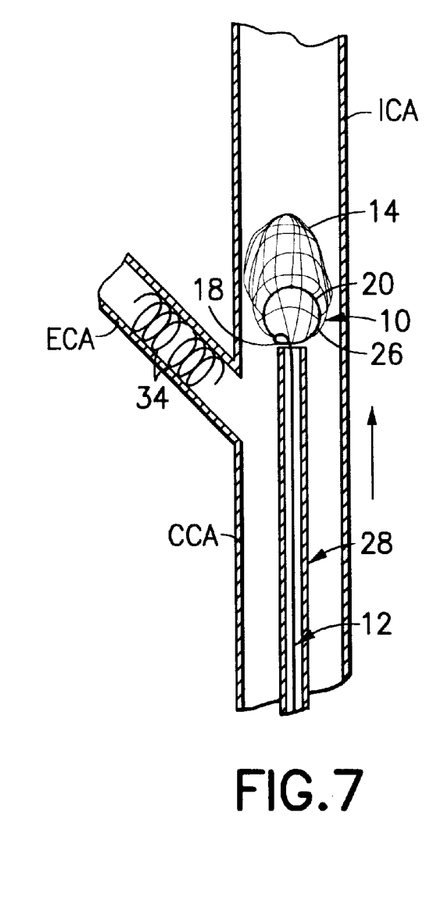

Having the ICA and the ECA blocked as required, an angioplasty balloon 36 may be introduced into the CCA to treat the stenosis S. The angioplasty balloon 36 is mounted to an angioplasty catheter 38 having a lumen 40 formed throughout. The angioplasty catheter 38, with the angioplasty balloon 36 being uninflated, is slid into the lumen 30 of the catheter 28 with the guidewire 12 of the filter 10 being threaded through the lumen 40 of the angioplasty catheter 38. The angioplasty catheter 38 is advanced through the catheter 28 until the angioplasty balloon 36 is aligned with the stenosis S. Thereafter, the angioplasty balloon 36 is inflated to compress the plaque forming the stenosis S, as shown in FIG. 6. Any embolus E which may be dislodged from the stenosis S will travel downstream with the flow of blood in the CCA and be trapped by the filter 10, or the embolus coils 34, if the embolus E is sufficiently large to be life-threatening. Once the stenosis S has been treated, the angioplasty balloon 36 is caused to return to the un-inflated state and the angioplasty catheter 38 is withdrawn. Thereafter, the physician pushes the catheter 28 in a distal direction relative to the guidewire 12, thereby collapsing the filter 10. As the catheter 28 is advanced, the straight segments 22 and 24 are pulled through the plane defined by the length 20 and into the lumen 30 of the catheter 28. Eventually, the loop 18 is drawn into pressing engagement with the distal end 32 of the catheter 28, as shown in FIG. 7. As the guidewire 12 is further withdrawn, the length 20 of the guidewire 12 passes through the loop 18 and into the catheter 28, with the connecting loops 26 being drawn together. Consequently, the filter 10 becomes fully collapsed with any trapped emboli being contained within the filter material 14. The guidewire 12 is withdrawn until the entire guidewire 12, including the loop 18 along with the filtering material 14, is retracted into the catheter 28. The catheter 28 is then withdrawn from the patient's body. Any secondary filter 10 which may be used is removed in a similar method.

Figure 8:
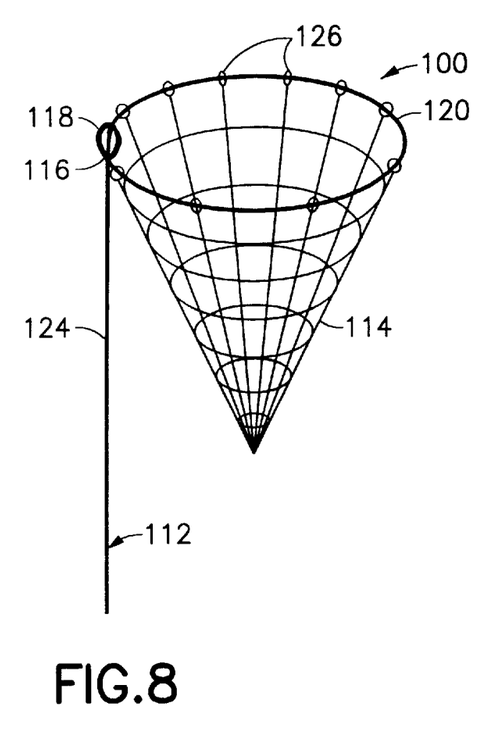
FIG. 8 is a front plan view of the filter of the second embodiment of the invention.
Figure 9:
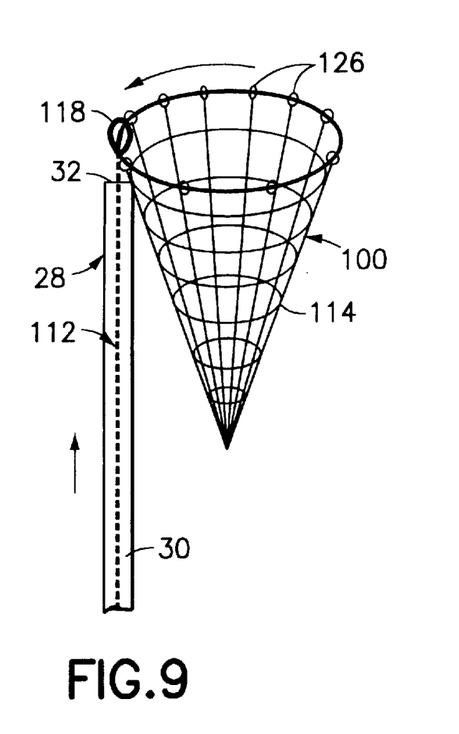
FIG. 9 is a view similar to FIG. 8, but including a catheter and showing the method of collapsing the filter of the second embodiment of the invention.
Figure 10:
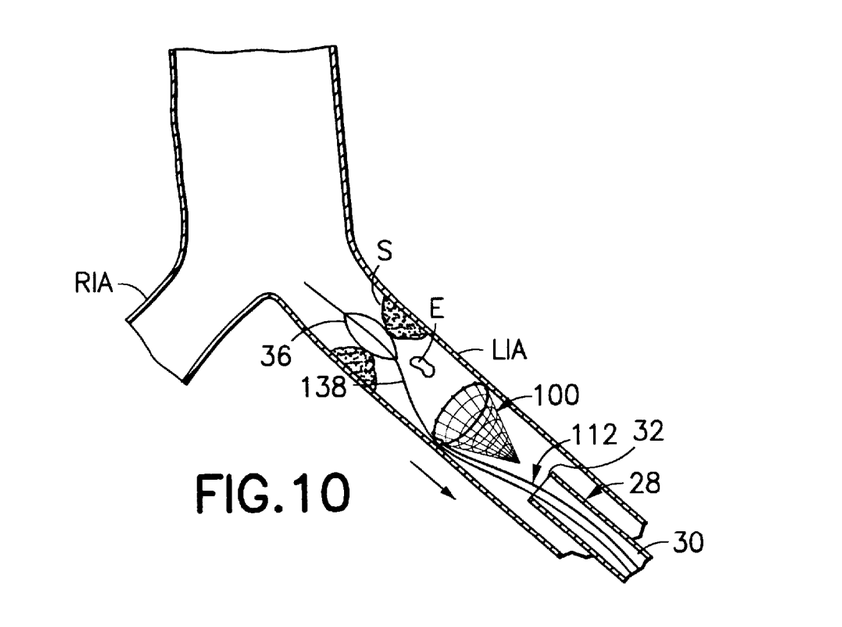
FIG. 10 is a diagrammatic representation of treating a stenosis in the left iliac artery using the second embodiment of the invention.

A second embodiment of the invention is formed to be introduced into a bloodstream in an upstream direction. Referring to FIGS. 8–10, a filter 100 is shown formed from a bent guidewire 112 and filtering material 114. The guidewire 112 and the filtering material 114 include exactly the same characteristics as those described with respect to the first embodiment of the invention. The guidewire 112 includes a distal end 116 bent and secured to a point on the guidewire 112 to define a loop 118. A length 120 extends from the loop 118 and into the loop 118 in a hitch configuration, as shown in FIG. 8. The guidewire 112 also includes a straight segment 124 which extends from the length 120. The length of the segment 124 must be greater than the length of the introducer catheter which is intended to be used with the filter 100. The filtering material 114 is connected to the length 120 of the guidewire 112 in a similar fashion to the way the filtering material 14 is connected to the guidewire 12 in the first embodiment of the invention. Namely, a plurality of connecting loops 126 may be provided with the filtering material 114 with the length 120 being threaded through each thereof, or a continuous hem (not shown) can be formed along the edge of the filtering material 114 with the length 120 passing therethrough. As with the first embodiment of the invention, the length 120 can be adjusted through the loop 118 through manipulation of the straight segment 124, resulting in bunching or expansion of the filtering material 114, accordingly. In contrast to the first embodiment of the invention, the filtering material 114 is directed coextensively with the straight segment 124 of the guidewire 112. FIG. 8 shows the relaxed state of the filter 100.

As an example of how the filter 100 is utilized, FIG. 10 depicts an illustration of an endovascular treatment of a stenosis S. The filter 100 is introduced into the bloodstream with the catheter 28 advancing in an upstream direction relative to the stenosis S to be treated. The stenosis S is shown to be formed in the left iliac artery LIA adjacent the branch connection with the right iliac artery RIA. The same type of introducer catheter 28, described with respect to the first embodiment of the invention, can be utilized having the lumen 30 formed throughout the entire length thereof, and the distal end 32. The arrow adjacent the LIA shows the direction of blood flow. To treat the stenosis S, the distal end of the catheter 28 is located slightly downstream of the stenosis S in the LIA. An angioplasty balloon 36, mounted on a guidewire 138, is passed through the lumen 30 of the catheter 28 and into alignment with the stenosis S. Thereafter, the filter 100 is passed through the catheter 28 by manipulation of the straight segment 124 of the guidewire 112. The filter 100 is in a collapsed state when passing through the catheter 28, with the filtering material 114 extending in the same direction as the flow of blood. With the filter 100 clearing the distal end of the catheter 28, the resiliency of the guidewire 112 causes the filter 100 to achieve its relaxed state. Similar to the first embodiment of the invention, the length 120 of the guidewire 112 comes into pressing engagement with the wall of the LIA, as shown in FIG. 10, and maintains the filter 100 at a fixed location. As with the first embodiment, the length 120 must be formed such that, in the relaxed state, a generally circular shape is defined with a diameter slightly greater than the inner dimension of a blood vessel.

With the filter 100 in an open configuration, as shown in FIG. 10, the guidewire 138 of the angioplasty balloon 36 is pressed against the wall of the LIA by the length 120 of the filter 100. The angioplasty balloon 36 is inflated and the stenosis S is treated. Any embolus E generated during the treatment of the stenosis S flows downstream and is trapped by the filtering material 114 of the filter 100, if sufficiently large to be life-threatening. Once treatment of the stenosis S is completed, the catheter 28 is advanced into the bloodstream with the distal end 32 coming into engagement with the loop 118, as shown in FIG. 9. With the catheter 28 being then rigidly maintained, the guidewire 112 is withdrawn through the catheter 28 with the length 120 decreasing. As a result, the filter 100 is eventually collapsed with the connecting loops 126 being drawn together. The entire filter 100 is then withdrawn into the catheter 28, with all trapped emboli being carried away therewith. Afterwards, the angioplasty balloon 36 and the catheter 28 are also removed.

Figure 11:
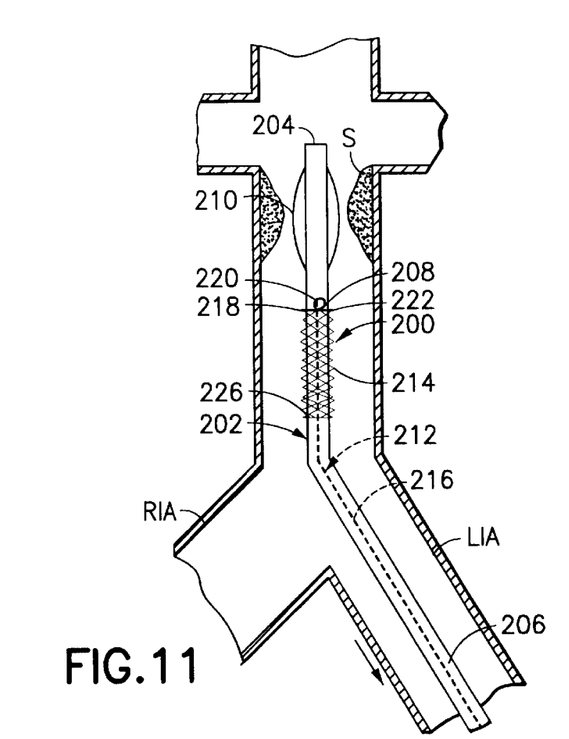
FIGS. 11–12 show the third embodiment of the invention as diagrammatic representations of treating a stenosis in the abdominal aorta.
Figure 12:
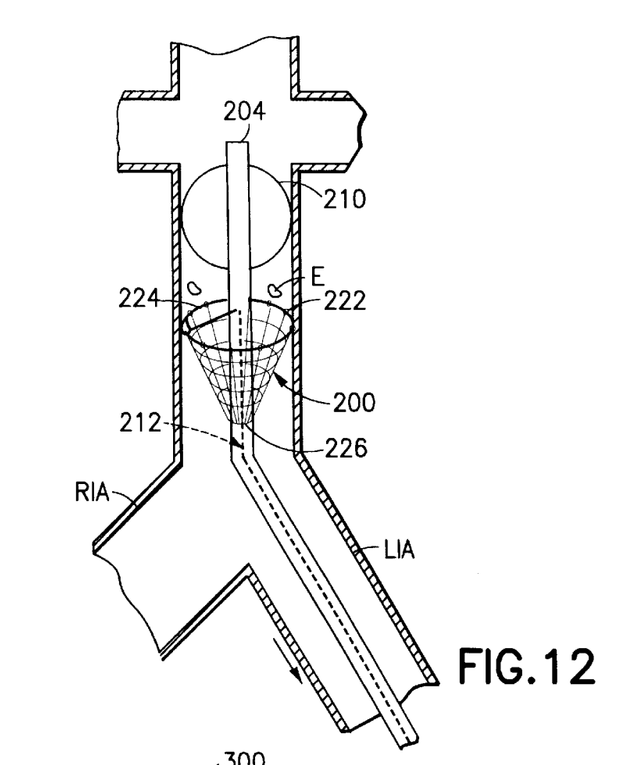

Referring to FIGS. 11–12, a third embodiment of the invention is depicted therein. A filter 200 is provided which is mounted onto an angioplasty catheter 202. The angioplasty catheter 202 is formed with a distal end 204 and a lumen 206 extending throughout the entire length thereof. An aperture 208 is formed through the wall of the angioplasty catheter 202 which is in communication with the lumen 206. An inflatable angioplasty balloon 210 is provided intermediate the distal end 204 and the aperture 208 of the angioplasty catheter 202.

The filter 200 is formed from a guidewire 212 and a filtering material 214, each having the same characteristics as the guidewire 12 and 112 in the filtering material 14 and 114 of the previous embodiments. The guidewire 212 includes a segment 216 which is disposed within the lumen 206 of the angioplasty catheter 202 and is formed to extend from the proximal end of the angioplasty catheter 202. The guidewire 212 is disposed to extend through the aperture 208 and about the circumference of the angioplasty catheter 202. The guidewire includes a distal end 218 which is bent and secured to a point on the guidewire 212 to define a loop 220. A length 222 of the guidewire extends from and into the loop 220 in a hitch configuration. The segment 216 extends from the length 222. Referring to FIG. 12, the guidewire 212, which is resilient, is formed to have a relaxed state, wherein the length 222 defines a generally circular shape having a diameter slightly greater than the inner dimension defined by a typical blood vessel. The filtering material 214 may be provided with a plurality of connecting loops 224, as shown in FIG. 12, with the length 222 being threaded therethrough. Alternatively, the filtering material 214 may include a continuous hem (not shown) with the length 222 passing therethrough. The filtering material 214 is also securely fixed to a circumference 226 of the angioplasty catheter 202, which is spaced from the aperture 208 in a proximal direction along the length of the angioplasty catheter 202. As shown in FIG. 11, the withdrawal of the guidewire 212 relative to the angioplasty catheter 202 in a proximal direction causes the length 222 to be drawn through the aperture 208 and the filter 200 to be forced into a collapsed state.

As an example of a possible use, the filter 200 and the angioplasty catheter 202, as shown in FIGS. 11 and 12, can treat a stenosis S where the angioplasty catheter 202 is introduced in an upstream direction relative to the flow of blood. The stenosis S is shown to be formed in the abdominal aorta. The angioplasty catheter 202 is introduced in an upstream direction through a femoral puncture site with the angioplasty balloon being aligned with the stenosis S for treatment. During advancement of the angioplasty catheter 202 throughout the bloodstream, the guidewire 212 is maintained in a taut position, such that the filter 200 is collapsed as shown in FIG. 11. With the angioplasty balloon 210 being in the desired location, the guidewire 212 is released from the taut position, thereby allowing the filter 200 to assume its relaxed state. As shown in FIG. 12, the length 222 comes into pressing engagement with the wall of the abdominal aorta. The angioplasty balloon 210 is actuated to treat the stenosis S and each embolus E which may result therefrom is trapped by the filter 200. Upon completion of treatment, the guidewire 212 is withdrawn through the lumen 206 of the angioplasty catheter 202, thereby causing the filter 200 to collapse about the angioplasty catheter 202, with each of the trapped emboli E being captured therein.

Figure 13:
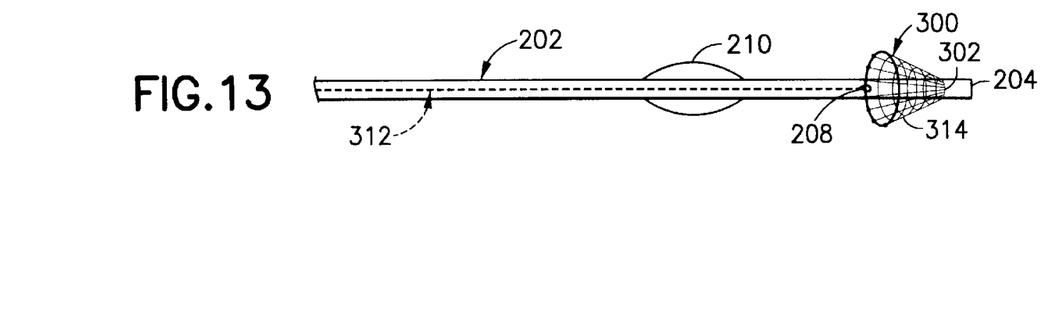
FIG. 13 is a plan view of the fourth embodiment of the invention.

As a modification of the third embodiment, a fourth embodiment of the invention is provided, wherein a filter 300 is mounted to the angioplasty catheter 202 for downstream introduction into a bloodstream. Here, the aperture 208 is formed intermediate the distal end 204 and the angioplasty balloon 210. The filter 300 includes a guidewire 312 which is formed exactly as the guidewire 212 of the third embodiment and disposed on the angioplasty catheter 202 also in the same manner. Filtering material 314 is mounted to the guidewire 312 and a circumference 302 which is adjacent the distal end 204. The operation of the fourth embodiment is exactly the same as the third embodiment, except that the angioplasty catheter 202 is introduced in a downstream direction.

As can be readily appreciated, the embodiments of the invention can be utilized in any form of endovascular treatment or simply for blood filtering, and is not limited to treatment of stenoses.

What is claimed is:

1. A filter for trapping emboli during endovascular procedures in a blood vessel, said filter comprising:
    a flexible guidewire having a first end, a second and and an intermediate portion extending therebetween, said intermediate portion including a first segment, a second segment and a unitary connection therebetween, said first segment extending a predetermined distance from said first end, said first segment being bent with said first end being secured to said unitary connection, said first segment defining a loop, said second segment extending from and through said loop; and
    a porous filtering material having interstices dimensioned to prevent passage therethrough of life-threatening emboli, said filtering material being slidably connected along a first length of said second segment, wherein said first length of said second segment is disposed in a plane transverse to other portions of said second segment.

2. A filter as in claim 1, wherein said first length of said second segment being formed to define a generally circular shape extending from and into said loop.

3. A filter as in claim 2, wherein said second segment being formed with a generally straight second length extending from said first length of said second segment, said second segment being formed with a generally straight third length extending from said second length and through said generally circular shape defined by said first length of said second segment, said second and said third lengths defining an acute angle therebetween.

4. A blood filtering system for trapping emboli in a blood vessel during endovascular treatment, said system comprising:
    a tubular catheter having a distal end for insertion into the blood vessel to be treated, said catheter defining a lumen along the entire length thereof;
    a guidewire slidably disposed in said lumen of said catheter, said guidewire having a first end, a second end and an intermediate portion extending therebetween, said intermediate portion including a first segment, a second segment and a unitary connection therebetween, said first segment extending a predetermined distance from said first end, said first segment being bent with said first end being secured to said unitary connection, said first segment defining a loop, said second segment extending from and through said loop, said second segment extending in a direction away from said distal end of said catheter; and
    a porous filtering material having interstices dimensioned to prevent passage therethrough of life-threatening emboli, said filtering material being slidably connected along a length of said second segment, wherein said guidewire and said filtering material collectively form a collapsible filter, said filter being reversibly collapsible between a relaxed state and a collapsed state, wherein, in said relaxed state, said filter being opened with a length of said second segment shaped and dimensioned for pressing engagement with the blood vessel, and, wherein, in said collapsed state, said filter being closed and capable of sliding passage through said lumen of said catheter.

5. A system for endovascular treatment of a blood vessel, said system comprising:
    a tubular catheter having a distal end for insertion into the blood vessel to be treated, said catheter defining a lumen along the entire length thereof;
    a guidewire slidably disposed in said lumen of said catheter, said guidewire having a first end, a second end and an intermediate portion extending therebetween, said intermediate portion including a first segment, a second segment and a unitary connection therebetween, said first segment extending a predetermined distance from said first end, said first segment being bent with said first end being secured to said unitary connection, said first segment defining a loop, said second segment extending from and through said loop, said second segment extending in a direction away from said distal end of said catheter;

a porous filtering material having interstices dimensioned to prevent passage therethrough of life-threatening emboli, said filtering material being slidably connected along a length of said second segment, wherein said guidewire and said filtering material collectively form a collapsible filter, said filter being reversibly collapsible between a relaxed state and a collapsed state, wherein, in said relaxed state, said filter being opened with a length of said second segment shaped and dimensioned for pressing engagement with the blood vessel, and, wherein, in said collapsed state, said filter being closed and capable of sliding passage through said lumen of said catheter; and an endovascular treatment device slidably disposed on said guidewire for endovascular treatment of the blood vessel.

6. A system as in claim 5, wherein said endovascular treatment device includes an angioplasty balloon.

7. A system as in claim 5, wherein said endovascular treatment device includes a stent.

8. A blood filtering system for trapping emboli in a blood vessel during endovascular treatment, said system comprising:

a tubular catheter having a proximal end and a distal end, said distal end for insertion into the blood vessel to be treated, said catheter being formed with a continuous cylindrical wall extending between said ends, said wall defining a lumen along the entire length of said catheter, wherein an aperture is formed through said wall in proximity to said distal end, said aperture defining a passage extending through said wall and in communication with said lumen;

a guidewire having a first end, a second end and an intermediate portion extending therebetween, said second end of said guidewire being located proximally the proximal end of said catheter, said intermediate portion of said guidewire including a first segment, a second segment and a unitary connection therebetween, said first segment extending a predetermined distance from said first end, said first segment being bent with said first end being secured to said unitary connection of said intermediate portion, said first segment defining a loop, said loop being disposed at a location external to said catheter, wherein said second segment extends continuously from said loop, through said loop, through said aperture, into said lumen, and to said second end of said guidewire; and a porous filtering material having interstices dimensioned to prevent passage therethrough of life-threatening emboli, said filtering material being slidably connected along a length of said second segment, said filtering material also being secured to a portion of said wall of said catheter.

9. A system as in claim 8, wherein said filtering material is secured to said wall of said catheter at locations intermediate said distal end of said catheter and said aperture.

10. A system as in claim 8, wherein said filtering material is secured to said wall of said catheter at locations intermediate said proximal end of said catheter and said aperture.

11. A system as in claim 8, wherein an inflatable angioplasty balloon is mounted to said wall of said catheter.

12. A filter for trapping emboli during endovascular procedures in a blood vessel, said filter comprising:

a flexible guidewire having a first end, a second end and an intermediate portion extending therebetween, said intermediate portion including a first segment, a second segment and a unitary connection therebetween, said first segment extending a predetermined distance from said first end, said first segment being bent with said first end being secured to said unitary connection, said first segment defining a loop, said second segment extending from and through said loop with a first length of said second segment being formed to define a generally circular shape extending from and into said loop; and a porous filtering material having interstices dimensioned to prevent passage therethrough of life-threatening emboli, said filtering material being slidably connected to said first length of said second segment, wherein said first length being dimensioned to be fully in pressing engagement with the blood vessel.

13. A filter for trapping emboli during endovascular procedures in a blood vessel, said filter comprising:

a flexible guidewire having a first end, a second end and an intermediate portion extending therebetween, said intermediate portion including a first segment, a second segment and a unitary connection therebetween, said first segment extending a predetermined distance from said first end, said first segment being bent with said first end being secured to said unitary connection, said first segment defining a loop, said second segment extending from and through said loop with a first length of said second segment being formed to define a generally circular shape extending from and into said loop, said second segment being formed with a generally straight second length extending from said first length of said second segment, said second segment being formed with a generally straight third length extending from said second length and through said generally circular shape defined by said first length of said second segment, said second and said third lengths defining an acute angle therebetween; and a porous filtering material having interstices dimensioned to prevent passage therethrough of life-threatening emboli, said filtering material being slidably connected to said first length of said second segment, wherein said first length being dimensioned for pressing engagement with the blood vessel.

* * * * *